United States Patent
Cuypers et al.

(10) Patent No.: US 9,981,057 B2
(45) Date of Patent: May 29, 2018

(54) SHEET-LIKE CARBON NANOTUBE-POLYMER COMPOSITE MATERIAL

(75) Inventors: Steven Cuypers, Gravenwezel (BE); Bogdan Bogdanov, Schoten (BE)

(73) Assignee: ORFIT INDUSTRIES, Wijnegem (BE)

( * ) Notice: Subject to any disclaimer, the term of this patent is extended or adjusted under 35 U.S.C. 154(b) by 502 days.

(21) Appl. No.: 14/001,918

(22) PCT Filed: Feb. 28, 2012

(86) PCT No.: PCT/IB2012/050928
§ 371 (c)(1),
(2), (4) Date: Nov. 6, 2013

(87) PCT Pub. No.: WO2012/117349
PCT Pub. Date: Sep. 7, 2012

(65) Prior Publication Data
US 2014/0052037 A1  Feb. 20, 2014

(30) Foreign Application Priority Data
Feb. 28, 2011 (BE) .................. 2011/0139

(51) Int. Cl.
| | |
|---|---|
| *A61L 15/12* | (2006.01) |
| *B82Y 30/00* | (2011.01) |
| *C08J 5/00* | (2006.01) |
| *C08K 3/04* | (2006.01) |
| *A61F 13/04* | (2006.01) |
| *A61B 90/18* | (2016.01) |
| *C08L 23/00* | (2006.01) |
| *C08L 67/04* | (2006.01) |
| *C08L 75/00* | (2006.01) |

(52) U.S. Cl.
CPC .............. *A61L 15/12* (2013.01); *A61B 90/18* (2016.02); *A61F 13/04* (2013.01); *B82Y 30/00* (2013.01); *C08J 5/005* (2013.01); *C08K 3/04* (2013.01); *C08K 2201/011* (2013.01); *C08L 23/00* (2013.01); *C08L 67/04* (2013.01); *C08L 75/00* (2013.01)

(58) Field of Classification Search
CPC ..... C08K 3/04; C08K 2201/011; C08L 23/00; C08L 67/04; C08L 75/00; A61B 2019/206; A61F 13/04; A61L 15/12; B82Y 30/00

USPC ............................................ 264/442; 602/7
See application file for complete search history.

(56) References Cited

FOREIGN PATENT DOCUMENTS

| | | |
|---|---|---|
| CN | 1 472 239 A | 2/2004 |
| WO | 96/11226 A2 | 4/1996 |

OTHER PUBLICATIONS

Jie-Feng Gao, et al., "CNTs/UHMWPE Composites With a Two-Dimensional Conductive Network", Materials Letters, Jul. 31, 2008, pp. 3530-3532, vol. 62, No. 20.
I.I. Konstantinov, et al., "Combining Carbon and Polymeric Particles in an Inert Fluid as a Promising Approach to Synthesis of Nanocomposites", Russian Journal of Applied Chemistry, Mar. 1, 2009, pp. 483-487, vol. 82, No. 3.
Rajagopal Ramasubramaniam, et al., "Homogeneous Carbon Nanotube/Polymer Composites for Electrical Applications", Applied Physics Letters, Oct. 6, 2003, pp. 2928-2930, vol. 83, No. 14.
Chan Luo, et al., "Flexible Carbon Nanotube—Polymer Composite Films with High Conductivity and Superhydrophobicity Made by Solution Process", Nano Letters, Dec. 10, 2008, pp. 4454-4458, vol. 8, No. 12.
Yuki Usui, et al., "Carbon Nanotubes with High Bone-Tissue Compatibility and Bone-Formation Acceleration Effects", Small, Feb. 1, 2008, pp. 240-246, vol. 4, No. 2.
D. Lahiri, et al., "Carbon Nanotube Reinforced Polylactide—Caprolactone Copolymer: Mechanical Strengthening and Interaction with Human Osteoblasts in Vitro", ACS Applied Materials and Interfaces, 2009, pp. 2470-2476, vol. 1, No. 11.

*Primary Examiner* — Janet L Epps-Smith
(74) *Attorney, Agent, or Firm* — Sughrue Mion, PLLC

(57) ABSTRACT

Use of a sheet-like composite material for the manufacture of an immobilization element, wherein the sheet-like composite material is made from a material comprising a thermoplastic polymer containing carbon nanotubes as a fibrous reinforcing material, obtainable by dispersing carbon nanotubes in a dispersing liquid in which the thermoplastic polymer does not dissolve, subjecting the dispersion to an ultrasonic treatment, adding of particles thermoplastic polymer to the dispersion and mixing of the thermoplastic polymer with the dispersion of carbon nanotubes, removing of the dispersing liquid, forming of the thermoplastic polymer impregnated with carbon nanotubes into a sheet.

18 Claims, 3 Drawing Sheets

SHEET-LIKE CARBON NANOTUBE-POLYMER COMPOSITE MATERIAL

CROSS REFERENCE TO RELATED APPLICATIONS

This application is a National Stage of International Application No. PCT/IB2012/050928 filed Feb. 28, 2012, claiming priority based on Belgian Patent Application No. 2011/0139 filed Feb. 28, 2011, the contents of all of which are incorporated herein by reference in their entirety.

The invention relates to the use of a sheet-like composite material comprising a thermoplastic polymer containing carbon nanotubes as a fibrous reinforcing material for the manufacture of an immobilization element for immobilization of at least a portion of a body part, according to the preamble of the first claim.

The use of fixation and immobilization elements or templates for immobilizing a part of a body has become well known technology in applications such as orthotics and prosthetics, physical rehabilitation, radiation oncology and diagnostic imaging. The possibility to mould the immobilization element directly on the patient is considered an important advantage, together with the mechanical properties and surface finishing. Besides that an immobilisation element which is light is observed as comfortable to the patient. For radiation oncology it is desired that the targeted body part may be immobilized in a precise and reproducible position with respect to the irradiation source, thereby leaving limited possibility to the immobilized body part to move with respect to the irradiation source. In particular when high precision treatments are involved—for example in Intensity Modulated Radiation Therapy, Image Guided Radiation Therapy, Stereotactic Radiation Therapy or Surgery—, or treatments with high energy, for example proton therapy, where the target is very well defined and delineated, the immobilization element should permit precise, highly accurate and reproducible re-positioning of the anatomical area of interest, and ensure that the possibility to move is limited to less than 2 mm to ensure that the radiation is delivered to the target, at minimum risk to exposure of surrounding healthy tissue. Other applications for immobilization elements include physical rehabilitation applications and orthopaedic applications for example in splints and braces, to immobilize and protect inflamed or injured joints, to support and immobilize ligaments and fractures and muscular structures and podiatry for example as insole (foot-bed) applications.

To produce fixation or immobilization elements, which are suitable for use in the above described applications, use is usually made of a sheet-like thermoplastic material, which is moulded to conform as good as possible to the body part that is to be immobilized. With high melting thermoplastics, a positive mould is used in the shape of the part that needs to be immobilized. Over the years, continuous development has been going on towards thermoplastic materials which may be directly moulded to the body part to be immobilized, as this permits achieving immobilization with the highest accuracy, where the size and shape of the immobilization elements may be directly adapted to each individual patient, in the position in which the body part is to be immobilized, and the size and shape may be adapted in the course of time by re-moulding the immobilization element. To permit this direct moulding, the thermoplastic material should have a melting temperature which is sufficiently low to be supported by the body.

Immobilization elements or templates of the type described above preferably have a bending modulus which is sufficiently high to minimize the risk to deformation of the element and the ability of the body part to move, provide a high stability during use of the immobilization element meaning that the ability of the body part to move in the immobilised state is restricted. To improve comfort and permit evaporation of moisture through the material, the material is often perforated, which however compromises rigidity of the material and stability of the immobilisation element.

The article "CNTs/UHMWPE composites with a two-dimensional conductive network" of J.-F. Gao, Z.-M. Li, Q.-J. Meng and Q. Yang in Materials Letters, 62 (2008) 3530-3532 discloses a process for the manufacture of a composite material comprising ultrahigh molecular weight polyethylene (UHMWPE), with the carbon nanotubes as a fibrous reinforcing material. The carbon nanotubes are dispersed in the alcohol with the aid of ultrasonic waves, and then the ultra-high molecular weight polyethylene in the form of granules are added to the dispersion. After evaporation of the alcohol the impregnated granules are processed into a composite material by compression molding.

The article "Combining Carbon and Polymeric Particles in an Inert Fluid as a Promising Approach to Synthesis of Nano Composites" of I. I. Konstantinov, V. V. Karbushev, A. V. Semakov and V. G. Kulichikhin from the Russian Journal of Applied Chemistry, 82 (2009) 489-493 describes a process for the manufacture of a composite material, comprising nano diamond dispersed in a polymer, selected from the group consisting of hydroxypropyl cellulose, polysulfone and a copolymer of styrene and acrylonitrile (SAN). The nano diamonds are dispersed in an inert liquid by means of ultrasonic waves, and then the polymer is added to the dispersion in the form of granules. After evaporation of the inert liquid, the impregnated beads are processed into a composite material by extrusion.

CN1472239 discloses a process for the manufacture of a composite material comprising carbon nanotubes, dispersed in a polymer, selected from the group consisting of thermotropic liquid crystalline polyesters, polyethylene, polypropylene, polytetrafluoroethylene, polytrifluorochloroethyleen, PVC, Merlon, polymethyl methacrylate, polystyrene, poly formaldehyde, polyvinyl alcohol, polyamide, polyacrylic nitrile, and ABS resin. The carbon nanotubes are dispersed in a liquid using ultrasonic waves and then the polymer is added to the dispersion in the form of granules. After evaporation of the inert liquid, the impregnated beads are processed into a composite material by extrusion.

Ramasubramaniam Rajagopal et al describe in Applied Physics Letter 83, 14 (2003) composite films having a thickness of 10.2 um, made of polystyrene, or polycarbonate with a single walled carbon nanotubes with PPE functional groups. The article concludes that although the PPE functional groups are not covalently bound to the carbon nanotubes, the composite exhibits a much improved electrical conductivity and is suitable for mechanical and thermal applications due to the multifunctional nature of the carbon nanotubes.

According to D. Lahiri et al in Applied Materials and Interfaces, vol. 1, no 11, 2470-2476 (2009) copolymers of polylactide-caprolactone reinforced with carbon nanotubes in an amount up to 5 wt. % exhibit an increased modulus of elasticity by the reinforcement provided by the rigid CNT and an increased tensile strength. Due to the high tensile strength of the CNT, they form an effective reinforcing material for improving the mechanical properties of a poly-ε-caprolactone composite material on the condition that the interfacial bonding is good.

None of these publications, however, disclose that the composite material is obtained by the method described, is suitable for use as immobilization element for immobilization of body parts in a predetermined position.

Immobilization elements for the immobilization of body parts are often manufactured from a sheet-like thermoplastic material, which is shaped in such a way that it encloses as good as possible to the body part to be immobilized. The sheet-shaped thermoplastic material is preferably directly formed on the body part to be immobilized, because then the most accurate immobilization can be achieved and the size and shape of the immobilization element can be adjusted to the individual patient. This requires the use of a thermoplastic material having a sufficiently low melting temperature, and a material which at that temperature exhibits sufficient plasticity and elasticity to permit shaping. Examples of suitable sheet-like thermoplastic materials for the direct moulding on the body are, inter alia, polyurethane, transpolyisoprene, polyesters e.g. poly-ε-caprolactone or mixtures of two or more of these materials. In practice, the sheet-like thermoplastic material is heated in a hot water bath to melt the material, after which it is applied and formed on the body part to be immobilized.

The object of the present invention is to provide a method for producing an immobilization element using a sheet of a composite material.

This is achieved by the invention with the technical features of the characterizing part of the first claim.

Thereto, the invention is characterized by the use of a sheet-like composite material comprising a thermoplastic polymer containing carbon nanotubes as a fibrous reinforcing material, wherein the composite material is obtainable by the dispersion of carbon nanotubes in a dispersing liquid in which the thermoplastic polymer does not dissolve, exposing the dispersion to ultrasonic waves, adding particles of thermoplastic polymer to the dispersion, and then mixing, removing of the dispersing liquid, forming into sheets of the thermoplastic polymer impregnated with the carbon nanotubes.

The invention also relates to a sheet-like composite material comprising a thermoplastic polymer containing carbon nanotubes as the fibrous reinforcing material, wherein the composite material is obtained by dispersion of carbon nanotubes in a dispersing liquid in which the thermoplastic polymer does not dissolve, as described above.

The invention further relates to an immobilization element for immobilization of at least a part of a body part, wherein the immobilization element is manufactured from a material having a sheet-shaped composite material comprising a thermoplastic polymer with carbon nanotubes as a fibrous reinforcing material, wherein the composite material is obtained by dispersing carbon nanotubes are in a dispersing liquid in which the thermoplastic polymer does not dissolve, as described above.

The sheet-like composite material according to the invention combines a good electrical conductivity with a good thermal conductivity. This favorable combination can be achieved with a small amount of carbon nanotubes, which the inventors attribute to the good dispersion of the carbon nanotubes obtained with the method of the first claim. Carbon nanotubes are generally commercially available as aggregates of a multitude of tubes. By the ultrasonic treatment in the dispersion it is possible to disaggregate these aggregates in an efficient way. As a result, it is possible to bring about a fine distribution of carbon nanotubes in the dispersion and finally to achieve a fine distribution of the carbon nanotubes in the thermoplastic material. The presence of electrical conductivity properties allows the sheet-like composite material to be heated to a deformable sheet by applying an electric voltage to the material, and in other words, to heat the material in a direct manner. A direct heating offers the advantage over the conventional heating of the sheet in a hot water bath that the sheet after heating is cooling less rapidly as no heat is withdrawn from the sheet by evaporation of the water. Due to slower cooling, a longer period of time remains available for forming the sheet to the body part to be immobilized, to a form which corresponds to and connects to the shape of the body part to be immobilized, and which encloses the body part to be immobilized well. In forming the sheet, it is important that the sheet can take as well as possible the form of the body part to be immobilized, to enable an efficient immobilization. Because with the invention the cooling of the sheet proceeds more slowly, a longer time will remain available for forming the sheet, and this is made possible.

Other methods for the direct heating to obtain include heating in a gas atmosphere, for example in an oven with air or another gas.

The thickness of the sheet may vary within wide ranges. When using the composite material for an immobilization element for immobilization of a body part, the thickness will usually vary between 0.5 and 3.2 mm, preferably 0.5 and 2.0 mm, more preferably 0.8 and 1.5 mm, most preferably 1.1 and 1.3 mm. Often, a thickness of about 1.2 mm is used. When selecting the suitable thickness, the skilled person will ensure that the thickness is sufficiently large to satisfy the requirements for the intended use. For immobilization elements, the thickness is usually chosen such that the flexural modulus and strength end up within the required limits for that application, and that the cooling time of the composite material after being heated to its melting or softening temperature, is sufficiently long to allow forming at/around the body part to be immobilized. The favorable flexural modulus and strength of the sheet-like composite material make it possible to use sheets with a smaller thickness so that the comfort provided to the patient is improved, without thereby adversely affecting the stability of the immobilization element. Moreover, the above-described sheet thickness may be heated sufficiently uniformly by means of direct heating to ensure a good formability of the sheet.

The nature of the thermoplastic polymer used for the manufacture of the composite material of this invention is not critical to the invention. Preferably, however, the thermoplastic polymer is selected from the group of thermoplastic elastomers, thermoplastic polyurethane, thermoplastic polyisoprene, thermoplastic polyesters, thermoplastic polyolefins, polyvinyl chloride, polystyrene, or a mixture of two or more of these polymers. In addition, polymers are preferably chosen which have a relatively low softening temperature at which the material is deformable, so that they are particularly suitable for the manufacture of an immobilization element which is directly molded on the body part to be immobilized. The body part then serves as a direct mold for the immobilization element. The skilled person is able to select from the above group of materials, the most suitable material or mixture.

Examples of suitable thermoplastic polyolefins include polyethylene, polypolylene, or ethylene-propylene co-polymers. Examples of suitable thermoplastic polyesters include polyethylene vinyl acetate, polyacrylate or polymethacrylate, polymeric fatty acid esters, in particular, poly-ε-caprolactone. Poly-ε-caprolactone, for example, marketed by Perstorp (UK) (under the brandname Capa). Preferably, thermoplastic polyurethane, isotactic polypropylene, a copolymer of ethylene with 1-butene, a copolymer of ethylene with 1-octene, poly-ε-caprolactone, thermoplastic polyurethane that contains poly-ε-caprolactone, as well as a mixture of two or more of these materials is used. Poly-ε-caprolactone is particularly preferred because it has a low melting point and is moldable at temperatures which are tolerated by the human or animal body. The thermoplastic polymers are provided in the form of small particles having a particle size comprised between 0, 5 and 500 microns, preferably between 1 and 300 micrometers. The small particles of thermoplastic polymer can be obtained, for example by cryogenic grinding of the polymer or by any other means found suitable by the skilled person.

Within the context of this invention, the concentration of carbon nanotubes in the composite material can be varied within wide limits. Preferably, the concentration of carbon nanotubes is smaller than 2.0 wt. % relative to the weight of the composite material, preferably smaller than 1.5 wt. %, more preferably smaller than 1.0 wt. %. The inventors have found that an increased electrical and thermal conductivity is obtained at relatively low content of carbon nanotubes. Without wishing to be bound by this theory, they assume that this is due to the high degree of dispersion which is achieved with the carbon nanotubes according to this invention. The carbon nanotubes, which are available as aggregates of a plurality of nanotubes, disaggregate by an ultrasonic dispersion treatment in which an extremely fine distribution of the nanotubes can be obtained. In addition, it is possible to control the degree of dispersion by controlling the duration and intensity of the ultrasonic treatment. The amount of carbon nanotubes in order to achieve this desired effect and the concentration of carbon nanotubes that can be dispersed, depends on the nature of the thermoplastic polymer and the compatibility between both. Increasing the concentration above 2.0 wt. % does not necessarily lead to an increased electrical and thermal conductivity. Further increasing of the concentration may result in dispersion with a viscosity which renders further processing of the material extremely difficult.

Preferably, the concentration of carbon nanotubes is greater than 0.05 wt. %, preferably greater than 0.1 wt. %, more preferably greater than 0.25 wt. %. With a concentration of carbon nanotubes lower than 0.05 wt. %, there is a risk that the electrical and thermal conductivity is considered to be inadequate. The inventors have further found that, depending on the nature of the thermoplastic polymer, the electrical and thermal conductivity increase abruptly above a threshold concentration. Preferably, the concentration of carbon nanotubes in the composite material is at least equal to the threshold concentration.

Preferably, the thermoplastic polymer particles have a particle size between 1 and 300 μm, more preferably between 50 and 200 μm. The inventors have found that in the method used in this invention, the carbon nanotubes are absorbed and adsorbed on the surface of the thermoplastic polymer particles, so that the surface-volume ratio of the particles may be important. The inventors have established that for this application, the surface-volume ratio is optimal for a particle size of the thermoplastic polymer between 1 and 300 μm. Such particles are sufficiently large to ensure that the carbon nanotubes can be absorbed on it and on the other hand that these thermoplastic polymer particles are sufficiently small to enable good dispersion of the carbon nanotubes into the polymer. In the above-mentioned particle size there is thus sufficient surface area per volume unit of thermoplastic polymer made available for absorption of carbon nanotubes. The polymer will usually partially crystalline and partially non-crystalline. The inventors assume that in addition to surface adsorption, the carbon nanotubes with the above-mentioned dimensions are also able to penetrate the amorphous phase.

Within the scope of this invention both multi-walled and single-walled carbon nanotubes can be used. Preferably, the carbon nanotubes are multiwall carbon nanotubes as they are easier to produce than single-walled carbon nanotubes, which clearly reduces cost.

The dimensions of the carbon nanotubes can vary within wide limits, without thereby affecting the thermal and electric conductivity too much. Preferably, the multi-walled carbon nanotubes have an inner diameter of 0.5-15 nm, preferably 3-7 nm, an outer diameter of 1-50 nm, preferably 5 to 25 nm, and a length of up to 100 μm, preferably a maximum of 75 μm, more preferably up to 50 μm. The inventors have found that multi-walled carbon nanotubes of that size are easy to disperse, both in the dispersing liquids as well as in the thermoplastic polymers in which they are dispersed for the applications in this invention. The dimensions of the carbon nanotubes are aligned with the particle size of above-mentioned polymers nanotubes so that they are able to absorb well on the polymer particles.

For the production of the sheet-like composite material used in the immobilization element of this invention, any technique deemed suitable by the person skilled in the art can be used. Preferably the formation of the thermoplastic polymer impregnated by the carbon nanotubes to a sheet takes place by means of extrusion, in particular direct extrusion of the impregnated polymer of which the dispersing liquid is evaporated.

When producing the carbon nanotubes dispersion, carbon nanotubes are dispersed in a dispersing liquid in which the thermoplastic polymer does not dissolve. Preferably, the dispersing liquid in which the thermoplastic polymer does not dissolve, is selected from the group of PDMS, toluene, methanol, acetone, diethyl ether, DMF and cyclohexane. The skilled person will be able to make the correct combination of thermoplastic polymer particles and dispersing liquid that meets the requirements and the desired properties of the present invention. For example, the dispersing liquid must be chosen such that the carbon nanotubes are absorbed on the surface of the thermoplastic polymer particles.

According to this invention, a sheet-shaped composite material is used for producing an immobilization element for immobilization of a body part.

Carbon nanotubes are one of the carbon allotropes, which occur as one or several layers of graphite which are to be rolled up in the form of a cylinder. Carbon nanotubes can be formed with a single wall, with a double wall, or with multiple walls, depending on the number of layers of graphite which are rolled up. In the present invention are preferably multi-walled carbon nanotubes are used. Carbon nanotubes are marketed by Nanocyl, Bayer MaterialScience, Arkema, Inc. and CNT Cheap Tubes Inc. Carbon nanotubes can be commercially available in pure form, raw or functionalized. Impure carbon nanotubes could contain impurities such as amorphous carbon, pyrolytic carbon, carbon nanoparticles and carbon fibers that were not removed during purification.

Carbon nanotubes, suitable for the present invention, may or may not be functionalized with one or more organic substances. Where necessary, the surface of the nanotubes may be changed to improve compatibility with the thermoplastic polymer, in order to obtain a better dispersion. Surface modifications may for example comprise surface coating of the carbon nanotubes with organic functional groups, which are compatible with the thermoplastic polymer in which the nanotubes are to be dispersed. Surface modifications also comprise the coating of the carbon nanotubes with polyethylene, polypropylene or poly-ε-caprolactone.

To cause a disaggregation of the aggregated carbon nanotubes, the raw carbon nanotubes are dispersed in a dispersing liquid. The nature of the chosen dispersing liquid is not critical to this invention, and suitable examples are poly (dimethylsiloxane), toluene, ε-caprolactone, methanol, acetone, diethyl ether, dimethylformamide, cyclohexane, or water. Preferably, a dispersing liquid is selected that has a contact angle with the carbon nanotubes of less than 90° so that an optimum wetting of the carbon nanotubes by the dispersing liquid is possible. The dispersing liquid is further selected such that it does not dissolve the thermoplastic polymer. The skilled person is capable of suitably combining the carbon nanotubes and the dispersing liquid that is compatible with the thermoplastic polymer in which the nanotubes are contained.

By dispersing the nanotubes in the above described dispersing liquid and exposing the dispersion to ultrasonic treatment, a very fine particle distribution can be obtained. The ultrasonic waves can for example be generated for a dispersion on laboratory scale by means of an ultrasonic generator with a capacity of approximately 200 W and a probe with a point of about 12 mm in diameter. The skilled person is capable of adapting the capacity of the ultrasonic generator taking into account the amount of dispersion. The skilled person is also capable of adjusting the duration of exposure to ultrasonic waves taking into account the nature of the materials, the envisaged disaggregation of the carbon nanotubes and the desired degree of dispersion of the carbon nanotubes.

The nanotubes dispersed in the dispersing liquid, obtained after exposing the dispersion to ultrasonic waves, are mixed with the thermoplastic polymer particles in a finely divided state. The polymer particles have a particle size comprised between 0, 5 and 500 μm, preferably between 1 and 300 μm. Because of their mixing, the polymer particles are impregnated with the carbon nanotubes. After the polymer particles have been impregnated, the dispersing liquid is removed, for example by evaporation.

The composite material comprising a thermoplastic polymer impregnated with carbon nanotubes can be produced in any manner known to the skilled person. The production is preferably controlled in such a way that a fine and homogeneous distribution of the carbon nanotubes into the polymer will result. This can be achieved for example by extrusion, by melting the impregnated thermoplastic material at the appropriate temperature and then extruding it into a sheet, but other techniques may be used. The concentration of carbon nanotubes, dispersed in the thermoplastic polymer is generally less than 2.0 wt. %, preferably less than 1.5 wt. %, more preferably less than 1.0 wt. % but more than 0.05 wt. %, preferably more than 0.1 wt. %, more preferably more than 0.25 wt. %. The lower limit is determined by the minimum concentration required to obtain a sudden increase in the electrical conductivity, the upper limit by the value of the concentration at which the electrical conductivity of a plateau is reached.

For an immobilization element made of a composite material, the composite material can be used in the form of a single sheet or a plurality of aggregate sheets, wherein the aggregate sheets are preferably connected to each other, for example by melting, by means of adhesives, by the sheets physically connect to each other, as by stitching, stapling and the like.

The sheet-like composite material can be used as a solid sheet, but may also comprise a multiplicity of perforations, extending through the thickness of the sheet and improving the comfort. A perforated sheet is preferred because it is lighter and allows evaporation which increases the comfort of the patient. With perforations is meant a plurality of holes extending through the material of the sheet. When forming, the composite material will normally be stretched, and therefore, will stretch along the perforations, so that their dimensions increase. The perforations can be applied randomly or according to a certain pattern. The dimensions of the perforations in the composite material will usually be between 0.5 and 3.0 mm, preferably between 1 and 2 mm. The dimensions and pattern of the perforations will usually be chosen in such a way that the heat is kept inside the immobilization element, to provide sufficient time for cooling the composite material, in order to have enough time for the immobilization element to be formed.

The invention also relates to the use of a sheet-shaped composite material as described above for the manufacture of an immobilization element for the immobilization of a body part in a predetermined position. With immobilization element is meant for example, a splint for immobilizing a hand or a part of the hand, arm, or a part thereof, a leg or a part thereof, a foot or a part thereof, and, for example a mask for the immobilization of a head or any other part of the body. The immobilization element can if desired, also consist of two parts, wherein a first part which is provided to enable it to immobilize the body to be covered, is made from the above-described sheet-like composite material and the second part which is provided to attach the first part, for example to a support surface, is manufactured from a thermoplastic material or from a different plastic material.

The invention also relates to a process for the manufacture of an immobilization element for immobilization of a body part in a predetermined position, wherein the immobilization element is manufactured from a sheet-like composite material containing or consisting of carbon nanotubes, dispersed in a thermoplastic polymer, wherein the composite material is obtained by dispersion of carbon nanotubes in a dispersing liquid in which the thermoplastic polymer does not dissolve, by subjecting the dispersion to an ultrasonic treatment, adding particles of thermoplastic polymer to the dispersion and then mixing with the dispersion of carbon nanotubes, removing of the dispersing liquid, forming of the thermoplastic polymer impregnated by carbon nanotubes into sheets and forming of the sheet into an immobilization element.

To form the immobilization element in such a way that it is capable of immobilizing the body part, the sheet-like composite material according to the present invention is heated to a temperature which corresponds to the melting or softening temperature of the thermoplastic polymer, which is placed either on the body part to be immobilized or in a positive mold, and after formation the element is allowed to cool. The heating of the immobilization element can occur in the usual manner, namely by immersing the sheet-like composite material in a hot water bath until the thermoplastic polymer is melted. Heating can also happen by means of a so-called dry heating, wherein the immobilization element is heated in an oven at a suitable temperature, or by means of microwaves, or in a hot gas at the appropriate temperature. The good electrical and thermal conductivity allows the sheet-like composite material to be heated to a deformable sheet by applying an electric voltage to the material. This direct heating offers the advantage over the conventional heating of the sheet in a hot water bath that the sheet after heating is cooling less rapidly as no heat is withdrawn from the sheet by evaporation of the water, so that a longer period of time is available to form the sheet on the body in such a way that the body part to be immobilized can be tightly enclosed, in which there is a choice between an immobilization without allowing movement, or an immobilization in which limited movement is permitted.

The invention further relates to an immobilization element for the immobilization of a body part in a predetermined position, wherein the immobilization element has been manufactured by dispersion of carbon nanotubes in a dispersing liquid in which the thermoplastic polymer does not dissolve, subjecting the dispersion to a treatment with ultrasonic waves, adding particles of thermoplastic polymer to the dispersion, and then mixing with the dispersion of carbon nanotubes, the removal of the dispersing liquid, forming the thermoplastic polymer impregnated by carbon nanotubes into sheets, whereupon the sheet is formed into an immobilization element. Preferably, the sheet is heated to its melting or softening temperature prior to its forming. Preferably, the sheet is formed by application of the heated sheet on the body part to be immobilized, and forming of the sheet on the body part.

Preferred embodiments of the composite material are as described above.

The invention will now be further described with reference to exemplary embodiments.

EXAMPLE 1

Figure 1:
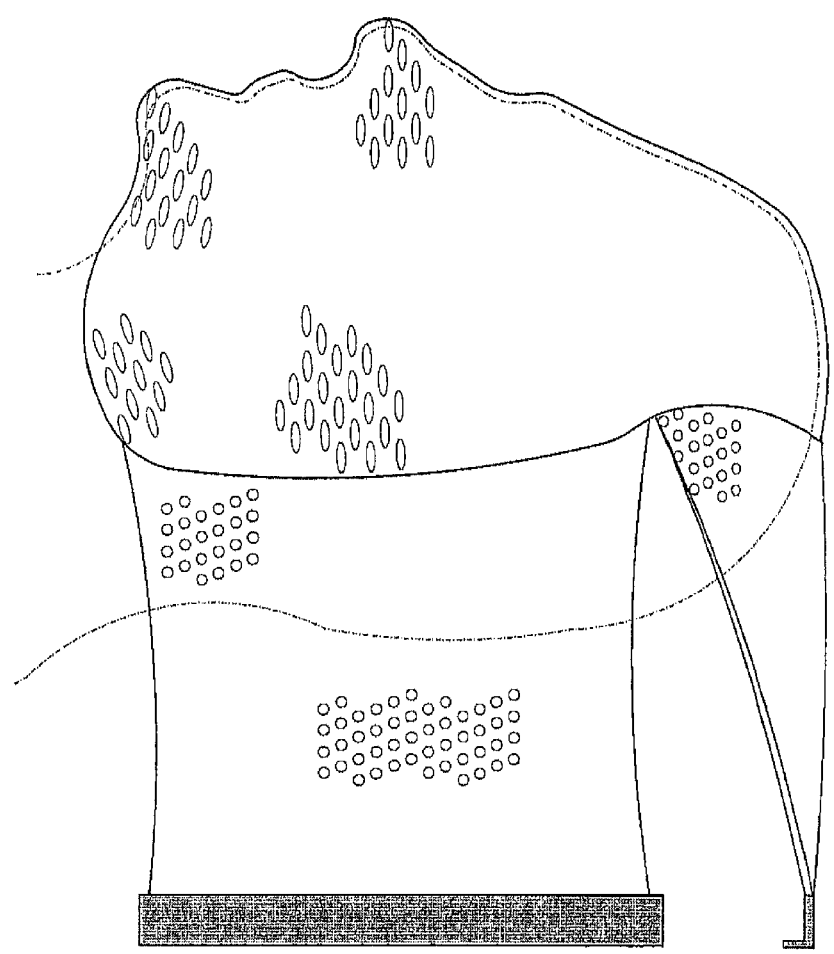
FIG. 1 shows an example of an apparatus for the immobilization of the head.
Figure 2:
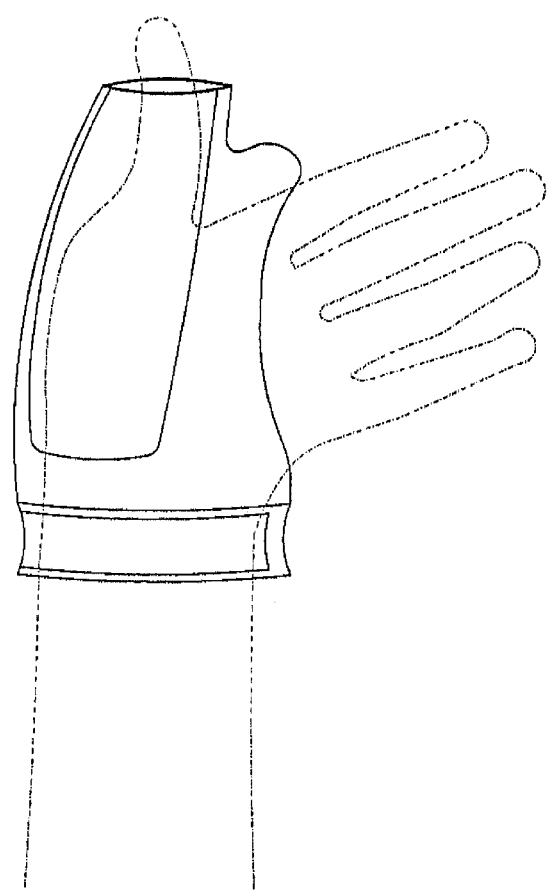
FIG. 2 shows an example of a splint for immobilizing a hand.
Figure 3:
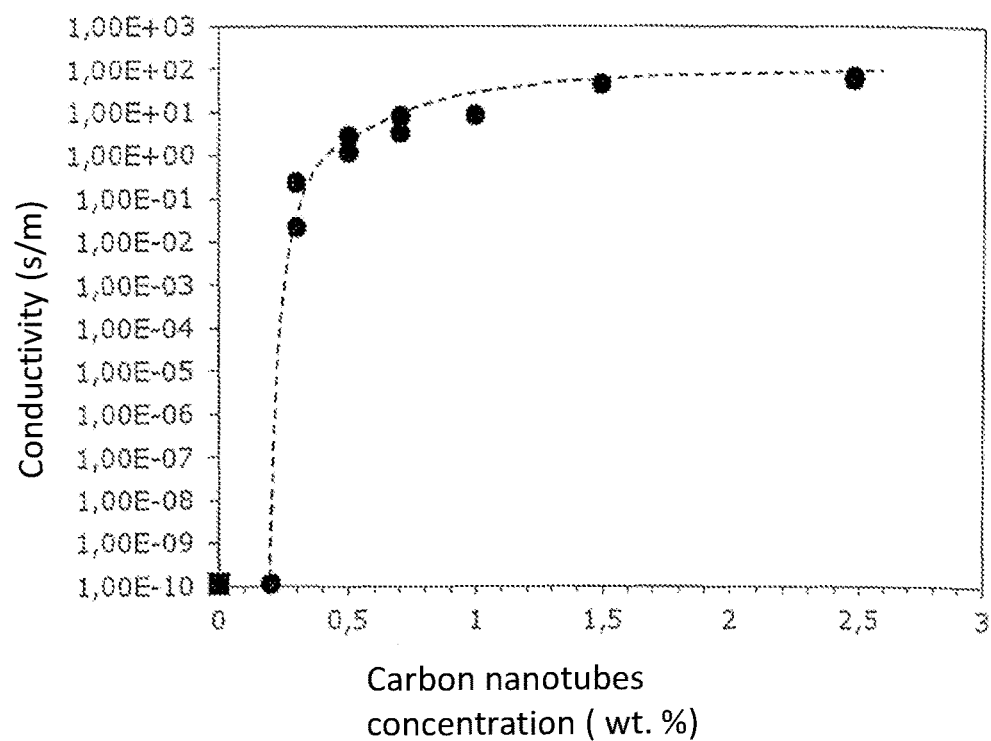
FIG. 3 shows a graph for the composite material sheets prepared in Example 1.

A sheet of a composite material was prepared by dispersing carbon nanotubes with various concentrations of 0.25 to 2.5 wt. %, as is clearly shown on the x-axis in FIG. 3, in poly-ε-caprolactone (Capa 6506) in powder form, obtained from Perstorp UK Ltd. The carbon nanotubes are multi-walled carbon nanotubes (Nanocyl 7000) of Nanocyl.

The carbon nanotubes were dispersed in diethyl ether, and the dispersion was subjected to ultrasonic waves. Poly-ε-caprolactone in the form of fine particles was mixed with the dispersion and the polymer particles were impregnated with the carbon nanotubes.

The composite material was produced by extruding the impregnated poly-ε-caprolactone particles in a ZSK 18 twin-screw extruder (Coperion) with a screw optimized for poly-ε-caprolactone nanocomposites (screw rotation speed 150 rpm, throughput rate 2 kg per hour). The composite material that was obtained in this way, was formed into a sheet by means of press molding at a temperature of 140° C. and a pressure of 100 bar, with a hydraulic press of Agila model PE30.

In order to evaluate the electrical conductivity, four-point conductivity measurements were carried out on the surface of the sheet-like composite material, with a Keithley 6512 programmable electronic meter (current range 1.1×10−6–1.1×2.10 A; voltage range 4.10-100 V). A colloidal graphite paste of Electron Microscopy Science was used to ensure fitting contact between the sample and the measuring electrodes. The results of these measurements are summarized in FIG. 3. The x-axis indicates the amount of carbon nanotubes, expressed in percent by weight with respect to the total weight of the composite material, and the y-axis the electrical conductivity, expressed in Siemens per meter.

The invention claimed is:

1. A method of making a non-invasive immobilization element for immobilizing a body part in a predetermined position, the immobilization element comprising a carbon nanotube-polymer composite material in the form of a sheet, the method comprising:
   dispersing carbon nanotubes in a dispersing liquid;
   subjecting the dispersion to an ultrasonic treatment;
   after the ultrasonic treatment, adding particles of a thermoplastic polymer to the dispersion and mixing the thermoplastic polymer particles with the dispersion of carbon nanotubes to impregnate the thermoplastic polymer particles with the carbon nanotubes;
   removing the dispersing liquid after impregnating the thermoplastic polymer particles with the carbon nanotubes;
   after removing the dispersing liquid, forming the thermoplastic polymer particles impregnated with carbon nanotubes into a sheet having a thickness of 0.5 to 3.2 mm;
   heating the sheet to a temperature corresponding to a melting or softening temperature of the thermoplastic polymer; and
   forming the immobilization element by placing the heated sheet on the body part to be immobilized or by placing the heated sheet in a positive mold in such a way that the body part to be immobilized can be tightly enclosed,
   wherein the thermoplastic polymer particles do not dissolve in the dispersing liquid;
   wherein the sheet is formed by means of extrusion, and wherein the thermoplastic polymer is poly-ε-caprolactone.

2. The method according to claim 1, characterized in that the thermoplastic polymer further comprises one or more selected from the group consisting of thermoplastic polyurethane, isotactic polypropylene, a copolymer of ethylene with 1-butene, and a copolymer of ethylene with 1-octene.

3. The method according to claim 1, characterized in that a concentration of carbon nanotubes in the sheet is smaller than 2.0 wt. % based on a total weight of the carbon nanotubes and thermoplastic polymer.

4. The method according to claim 1, characterized in that a concentration of carbon nanotubes in the sheet is greater than 0.05 wt. % based on a total weight of the carbon nanotubes and thermoplastic polymer.

5. The method according to claim 1, characterized in that the thermoplastic polymer particles added to the dispersion have a particle size between 1 and 300 μm.

6. The method according to claim 1, characterized in that the carbon nanotubes are multi-walled carbon nanotubes.

7. The method according to claim 1, characterized in that the dispersing liquid is selected from the group consisting of PDMS, toluene, methanol, acetone, diethyl ether, DMF and cyclohexane.

8. The method according to claim 1, wherein the sheet has a thickness of between 0.5 and 2.0 mm.

9. The method according to claim 1, wherein the sheet is subjected to direct heating, after which the sheet is formed.

10. The method according to claim 3, wherein the concentration of carbon nanotubes is smaller than 1.5 wt. %.

11. The method according to claim 3, wherein the concentration of carbon nanotubes is smaller than 1 wt. %.

12. The method according to claim 1, characterized in that the concentration of carbon nanotubes is greater than 0.1 wt. %.

13. The method according to claim 1, characterized in that the concentration of carbon nanotubes is greater than 0.25 wt. %.

14. The method according to claim 1, characterized in that the thermoplastic polymer particles added to the dispersion have a particle size between 50 and 200 μm.

15. The method according to claim 1, characterized in that the sheet has a thickness of between 0.8 and 1.5 mm.

16. The method according to claim 1, characterized in that the sheet has a thickness of between 1.1 and 1.3 mm.

17. The method according to claim 1, characterized in that the immobilization element is formed by placing the heated sheet on the body part to be immobilized.

18. The method according to claim 1, characterized in that the carbon nanotubes are homogenously distributed in the sheet of carbon nanotube-polymer composite material.

\* \* \* \* \*